United States Patent
Kubo et al.

(10) Patent No.: US 9,839,359 B2
(45) Date of Patent: Dec. 12, 2017

(54) FLUORESCENCE OBSERVATION APPARATUS

(71) Applicant: OLYMPUS CORPORATION, Tokyo (JP)

(72) Inventors: Kei Kubo, Tokyo (JP); Yasushige Ishihara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/046,860

(22) Filed: Feb. 18, 2016

(65) Prior Publication Data

US 2016/0157722 A1 Jun. 9, 2016

Related U.S. Application Data

(63) Continuation of application No. PCT/JP2014/068701, filed on Jul. 14, 2014.

(30) Foreign Application Priority Data

Aug. 23, 2013 (JP) .................................. 2013-173111

(51) Int. Cl.
*A61B 5/00* (2006.01)
*H04N 7/18* (2006.01)
(Continued)

(52) U.S. Cl.
CPC .......... *A61B 5/0071* (2013.01); *A61B 1/0005* (2013.01); *A61B 1/00009* (2013.01);
(Continued)

(58) Field of Classification Search
CPC .. G01N 21/64; A61B 5/0071; A61B 1/00009; A61B 1/043; A61B 1/0638; A61B 1/0646
(Continued)

(56) References Cited

U.S. PATENT DOCUMENTS

2007/0093691 A1 4/2007 Kobayashi
2011/0121200 A1 5/2011 Watanabe
(Continued)

FOREIGN PATENT DOCUMENTS

EP 2255717 A1 12/2010
EP 2564755 A1 3/2013
(Continued)

OTHER PUBLICATIONS

International Search Report dated Oct. 21, 2014 issued in PCT/JP2014/068701.
(Continued)

*Primary Examiner* — Carl H Layno
*Assistant Examiner* — Jon Eric C Morales
(74) *Attorney, Agent, or Firm* — Scully, Scott, Murphy & Presser, P.C.

(57) ABSTRACT

A fluorescence observation apparatus including a light source that radiates illumination light and excitation light; a return-light-image generating portion and a fluorescence-image generating portion that generate a return-light image and a fluorescence image, respectively; a fluorescence detecting portion that detects a fluorescence region in the fluorescence image; a return-light-image adjusting portion that adjusts gradation values of the return-light image; a superimposed-image generating portion that generates a superimposed image by using the return-light image, in which the gradation values have been adjusted, and the fluorescence image; and a coefficient setting portion that sets, in the case in which the fluorescence region is detected, a degree-of-reduction of the gradation values, so that the gradation values of the return-light image are decreased as compared with the case in which the fluorescence region is not detected.

7 Claims, 13 Drawing Sheets

(51) Int. Cl.
*A61B 1/00* (2006.01)
*A61B 1/04* (2006.01)
*A61B 1/045* (2006.01)
*G06T 5/50* (2006.01)
*G06T 5/00* (2006.01)
*G06T 19/00* (2011.01)
*G06T 19/20* (2011.01)
*A61B 1/06* (2006.01)

(52) U.S. Cl.
CPC .............. *A61B 1/043* (2013.01); *A61B 1/045* (2013.01); *G06T 5/008* (2013.01); *G06T 5/50* (2013.01); *G06T 19/006* (2013.01); *G06T 19/20* (2013.01); *A61B 1/0638* (2013.01); *A61B 1/0646* (2013.01); *G06T 2207/10064* (2013.01); *G06T 2207/10068* (2013.01); *G06T 2207/20212* (2013.01)

(58) Field of Classification Search
USPC .................. 348/135; 382/132; 600/109, 476
See application file for complete search history.

(56) References Cited

U.S. PATENT DOCUMENTS

| | | |
|---|---|---|
| 2012/0078046 A1 | 3/2012 | Sasaki et al. |
| 2013/0039562 A1 | 2/2013 | Watanabe |
| 2014/0184790 A1* | 7/2014 | Ishihara ............. A61B 1/00009 348/135 |
| 2015/0016705 A1* | 1/2015 | Kubo ................. A61B 1/00009 382/132 |

FOREIGN PATENT DOCUMENTS

| | | |
|---|---|---|
| EP | 2 979 611 A1 | 2/2016 |
| JP | H07-222712 A | 8/1995 |
| JP | 2003-010101 A | 1/2003 |
| JP | 2005-348902 A | 12/2005 |
| JP | 2007-111328 A | 5/2007 |
| JP | 3923595 B2 | 6/2007 |
| JP | 2009-226065 A | 10/2009 |
| JP | 2011-110216 A | 6/2011 |
| JP | 2012-070935 A | 4/2012 |
| JP | 2013-056001 A | 3/2013 |
| WO | WO 2011/135992 A1 | 11/2011 |

OTHER PUBLICATIONS

Extended Supplementary European Search Report dated Mar. 20, 2017 in European Patent Application No. 14 83 8502.4.

* cited by examiner

FLUORESCENCE OBSERVATION APPARATUS

CROSS-REFERENCE TO RELATED APPLICATIONS

This is a continuation of International Application PCT/JP2014/068701, with an international filing date of Jul. 14, 2014, which is hereby incorporated by reference herein in its entirety. This application claims the benefit of Japanese Patent Application No. 2013-173111, filed on Aug. 23, 2013, the content of which is incorporated herein by reference.

TECHNICAL FIELD

The present invention relates to a fluorescence observation apparatus.

BACKGROUND ART

In the related art, with regard to fluorescence observation apparatuses with which an affected site is diagnosed by using a fluorescent agent, there is a known method in which a region in a white-light image of biological tissue from which fluorescence is detected is displayed by replacing the region with a marker having a predetermined color. By doing so, an observer can reliably recognize the presence of the affected site in a viewing field. On the other hand, there is a problem in that it is not possible to observe the morphology of the affected site to which the marker has been applied. Furthermore, there is a problem in that a marker that is different in nature from the rest of the white-light image appears unnatural to the observer. In particular, by displaying, also with the marker, fine noise that is erroneously detected as fluorescence, the observer experiences a sense of flickering.

Thus, there is a known method in which a fluorescence image is displayed by being superimposed on a white-light image by allocating the fluorescence image in which fluorescence from the affected site is captured to one of R, G, and B component images that constitute the white-light image (for example, see Patent Literature 1). The superimposed image generated by this method includes information about the white-light image also in the region that corresponds to a fluorescence region in the fluorescence image. Therefore, it is possible to display the fluorescence region without hindering morphological observation of the affected site, and also, without giving the observer an unnatural impression or a sense of flickering. However, with the method of Patent Literature 1, in the case in which the fluorescence intensity is low relative to a bright return-light image like the white-light image, the visibility of the fluorescence region in the superimposed image may be poor.

Thus, there is a known method in which analog signals that express a fluorescence image and an illumination-light image, respectively, are obtained by receiving the fluorescence image and the illumination-light image by using a photoelectric conversion device and by subjecting these images to photoelectric conversion, and in which the analog signals representing the fluorescence image are amplified by a greater gain than the analog signals representing the illumination-light image (for example, see Patent Literature 2). The photoelectric conversion device and an AD conversion circuit that processes the analog signals generated by the photoelectric conversion device contain dynamic ranges. Therefore, in the case in which the fluorescence intensity is low relative to a bright illumination-light image, in some cases, it is difficult to ensure a sufficient gain for analog signals representing a fluorescence image to achieve a sufficient visibility of a fluorescence region in a superimposed image.

In addition, a means for displaying an image, such as a monitor or the like, also contains a dynamic range related to displaying. Therefore, in the case in which an illumination-light image is displayed on a monitor with a certain level of brightness, even if it were possible to ensure a sufficiently large gain for analog signals representing a fluorescence image, in some cases, it is not possible to display a fluorescence region with a sufficient brightness to ensure sufficient visibility of the fluorescence region in a superimposed image.

CITATION LIST

Patent Literature

{PTL 1} PCT International Publication No. WO 2011/135992
{PTL 2} Japanese Unexamined Patent Application, Publication No. 2003-10101

SUMMARY OF INVENTION

The present invention provides a fluorescence observation apparatus including a light source that radiates illumination light and excitation light onto a subject; a return-light-image generating portion that generates a return-light image in which return light emitted from the subject due to the irradiation with the illumination light from the light source is captured; a fluorescence-image generating portion that generates a fluorescence image in which fluorescence emitted from the subject due to the irradiation with the excitation light from the light source is captured; a fluorescence detecting portion that detects a fluorescence region having gradation values equal to or greater than a predetermined gradation value threshold in the fluorescence image generated by the fluorescence-image generating portion; a return-light-image adjusting portion that adjusts gradation values of the return-light image; a superimposed-image generating portion that generates a superimposed image in which the return-light image, in which the gradation values have been adjusted by the return-light-image adjusting portion, and the fluorescence image are superimposed; and a coefficient setting portion that sets a degree-of-reduction, by which the gradation values of the return-light image are adjusted by the return-light-image adjusting portion, based on the detection result of the fluorescence detecting portion for the fluorescence region, wherein, in the case in which the fluorescence region is detected by the fluorescence detecting portion, the coefficient setting portion sets the degree-of-reduction so that gradation values of the return-light image are decreased as compared with the case in which the fluorescence region is not detected by the fluorescence detecting portion.

DESCRIPTION OF EMBODIMENTS

First Embodiment

A fluorescence observation apparatus 100 according to a first embodiment of the present invention will be described below with reference to FIGS. 1 to 4.

Figure 1:
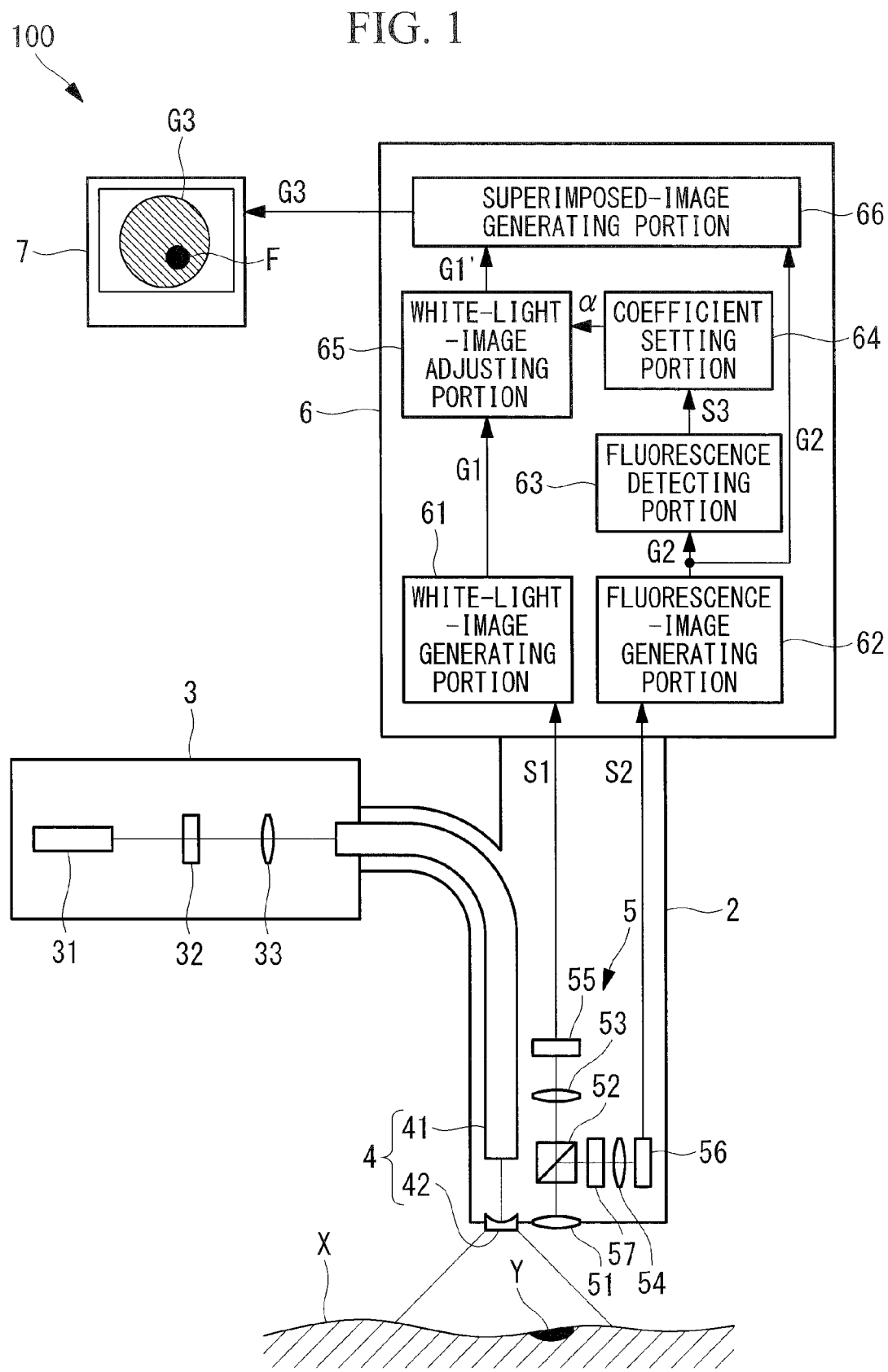
FIG. 1 is an overall configuration diagram of a fluorescence observation apparatus according to a first embodiment of the present invention.

As shown in FIG. 1, the fluorescence observation apparatus 100 according to this embodiment is an endoscope apparatus provided with an elongated inserted portion 2 that is inserted into a body, a light source 3, an illumination unit 4 that radiates excitation light and illumination light coming from the light source 3 toward an observation subject (subject) X from the distal end of the inserted portion 2, an image-acquisition unit 5 that is provided at the distal end of the inserted portion 2 and that acquires pieces of image information S1 and S2 about biological tissue, that is, the observation subject X, an image-processing unit 6 that is disposed at the base side of the inserted portion 2 and that processes the pieces of image information S1 and S2 acquired by the image-acquisition unit 5, and a monitor 7 that displays an image G3 processed by the image-processing unit 6.

The light source 3 is provided with a xenon lamp 31, a filter 32 that extracts the excitation light and the illumination light from light emitted from the xenon lamp 31, and a coupling lens 33 that focuses the excitation light and the illumination light extracted by the filter 32. The filter 32 selectively transmits light of a wavelength band from 400 nm to 740 nm, which corresponds to the excitation light and the illumination light. In other words, in this embodiment, near-infrared light (for example, the wavelength band from 700 nm to 740 nm) is used as the excitation light. Note that, instead of the xenon lamp 31, other types of lamp light sources or semiconductor light sources such as an LED or the like may be employed.

The illumination unit 4 is provided with a light-guide fiber 41 that is disposed over nearly the entire length of the inserted portion 2 in the longitudinal direction thereof and an illumination optical system 42 that is provided at the distal end of the inserted portion 2. The light-guide fiber 41 guides the excitation light and the illumination light focused by the coupling lens 33. The illumination optical system 42 spreads out and radiates the excitation light and the illumination light guided thereto via the light-guide fiber 41 onto the observation subject X facing the distal end of the inserted portion 2.

The image-acquisition unit 5 is provided with an objective lens 51 that collects light coming from the observation subject X, a dichroic mirror 52 that, of the light collected by the objective lens 51, reflects excitation light and fluorescence and transmits white light having a shorter wavelength (wavelength band from 400 nm to 700 nm, return light) than the excitation light, two focusing lenses 53 and 54 that focus the fluorescence reflected by the dichroic mirror 52 and the white light transmitted through the dichroic mirror 52, respectively, an image-acquisition device 55, such as, a color CCD that captures the white light focused by the focusing lens 53, and an image-acquisition device 56 like a high-sensitivity monochromatic CCD that captures the fluorescence focused by the focusing lens 54. In the figures, reference sign 57 is an excitation-light cut filter that, of the light reflected by the dichroic mirror 52, selectively transmits the fluorescence (for example, the wavelength band from 760 nm to 850 nm) and blocks the excitation light.

Although the image-acquisition device 55 for the white light and the image-acquisition device 56 for the fluorescence may be of different types from each other, as described above, they may be of the same type.

The image-processing unit 6 is provided with a white-light-image generating portion (return-light-image generating portion) 61 that generates a white-light image (return-light image) G1 based on the white-light-image information S1 acquired by the image-acquisition device 55, a fluorescence-image generating portion 62 that generates a fluorescence image G2 based on the fluorescence-image information S2 acquired by the image-acquisition device 56, a fluorescence detecting portion 63 that detects a fluorescence region F in the fluorescence image G2 generated by the fluorescence-image generating portion 62, a coefficient setting portion 64 that sets a coefficient α related to gradation values of the white-light image G1 based on the detection result of the fluorescence detecting portion 63, a white-light-image adjusting portion (return-light-image adjusting portion) 65 that generates an adjusted image G1' by adjusting the gradation values of the white-light image G1 based on the coefficient α, and a superimposed-image generating portion 66 that generates a superimposed image G3 by superimposing the fluorescence image G2 on the adjusted image G1'.

The fluorescence detecting portion 63 holds a predetermined threshold Th for the gradation values of the fluorescence image G2. The fluorescence detecting portion 63 compares the gradation values of individual pixels of the fluorescence image G2 input from the fluorescence-image generating portion 62 with the threshold Th, and detects the pixels having gradation values equal to or greater than the threshold Th as the fluorescence region F. The fluorescence detecting portion 63 outputs, to the coefficient setting portion 64, signals S3 indicating whether or not the fluorescence region F have been detected.

The coefficient setting portion 64 holds two predetermined values α1 and α2 as the coefficient α, selects the value α1 or the value α2 in accordance with the signals S3 received from the fluorescence detecting portion 63, and outputs the selected value to the white-light-image adjusting portion 65. Here, α1=1 and 0<α2<1 (for example, α2=0.6). The coefficient setting portion 64 selects α2 in the case in which the signals indicating that the fluorescence region F have been detected are received from the fluorescence detecting portion 63. On the other hand, the coefficient setting portion 64 selects α1 in the case in which the signals indicating that the fluorescence region F have not been detected are received from the fluorescence detecting portion 63.

Expression (1) below expresses processing for generating the superimposed image G3 by using the white-light image G1 and the fluorescence image G2, which is performed by the white-light-image adjusting portion 65 and the superimposed-image generating portion 66. In Expression (1), R, G, and B are gradation values of red (R) components, green (G) components, and blue (B) components of the individual pixels of the white-light image G1, FL is gradation values of the individual pixels of the fluorescence image G2, and R', G', and B' are gradation values of R components, G components, and B components of the individual pixels of the superimposed image G3. The white-light-image adjusting portion 65 and the superimposed-image generating portion 66 apply the processing of Expression (1) to all pixels in the white-light image G1 and the fluorescence image G2.

{Eq. 1}
$$\begin{pmatrix} R' \\ G' \\ B' \end{pmatrix} = \begin{pmatrix} a & 0 & 0 & 0 \\ 0 & a & 0 & 1 \\ 0 & 0 & a & 0 \end{pmatrix} \begin{pmatrix} R \\ G \\ B \\ FL \end{pmatrix} \quad (1)$$

Describing the processing expressed by Expression (1) more specifically, the white-light-image adjusting portion 65 multiplies the gradation values of the individual color components of the individual pixels of the white-light image G1 by the coefficient α set by the coefficient setting portion 64, thus calculating the gradation values of the individual color components of the individual pixels of the adjusted image G1'. The superimposed-image generating portion 66 adds the monochromatic fluorescence image G2 to one of the three color component images (i.e., the red (R) component image, the green (G) component image, and the blue (B) component image) that constitute the adjusted image G1' having colors. Then, the superimposed-image generating portion 66 reconstructs the superimposed image G3 having colors by using the color component image to which the fluorescence image G2 has been added and the other two color component images.

With the above-described processing, in the case in which the coefficient α is α1 (=1), the white-light image G1 serves as the adjusted image G1' without modification. In other words, the superimposed image G3 is generated based on the white-light image G1 having the original gradation values. On the other hand, in the case in which the coefficient α is α2, a white-light image G1 in which the gradation values are decreased is generated as an adjusted image G1', and the superimposed image G3 is generated based on this adjusted image G1'. With such processing, it is possible to adjust the gradation values of the white-light image G1 by using only the computational processing, and thus, it is possible to simplify the apparatus configuration. In this superimposed image G3, the observer can perform observation by associating the morphology of the subject X and the fluorescence region F with each other. In addition, because the superimposed image G3 includes information about the white-light image G1 also in the region in which the fluorescence region F is superimposed, it is possible to observe the morphology of the subject X in the region corresponding to the fluorescence region F.

The superimposed image G3 generated in accordance with Expression (1) is an image in which red, green, or blue fluorescence region F is displayed superimposed on the adjusted image G1'. In this embodiment, because the hue of biological tissue, that is, the observation subject X, includes a large amount of R components, it is preferable that the color in which the fluorescence region F is displayed in the superimposed image G3 be green, which is the complementary color of red. Therefore, the matrix in Expression (1) is set so that the fluorescence region F is allocated to the G component image of the adjusted image G1'.

Next, the operation of the thus-configured fluorescence observation apparatus 100 will be described.

In order to observe the biological tissue, that is, the observation subject X, in the body by using the fluorescence observation apparatus 100 according to this embodiment, a fluorescent substance that accumulates in an affected site Y is administered to the observation subject X in advance. Then, the inserted portion 2 is inserted into the body, and the distal end of the inserted portion 2 is disposed so as to face the observation subject X. Subsequently, the light source 3 is activated to radiate the excitation light and the illumination light onto the observation subject X from the distal end of the inserted portion 2.

In the observation subject X, the fluorescent substance contained in the affected site Y is excited by the excitation light, thus emitting fluorescence, and the white light is reflected at the surface of the observation subject X. A portion of the fluorescence emitted from the observation subject X and a portion of the white light reflected thereat return to the distal end of the inserted portion 2 and are collected by the objective lens 51.

Of the light collected by the objective lens 51, the white light is transmitted through the dichroic mirror 52, is focused by the focusing lens 53, and is acquired by the image-acquisition device 55 as the white-light-image information S1. On the other hand, the fluorescence collected by the objective lens 51 is reflected at the dichroic mirror 52, is focused by the focusing lens 54 after the excitation light is removed therefrom by the excitation-light cut filter 57, and is acquired by the image-acquisition device 56 as the fluorescence-image information S2. The pieces of image information S1 and S2 acquired by the individual image-acquisition devices 55 and 56 are transmitted to the image-processing unit 6.

Figure 2:
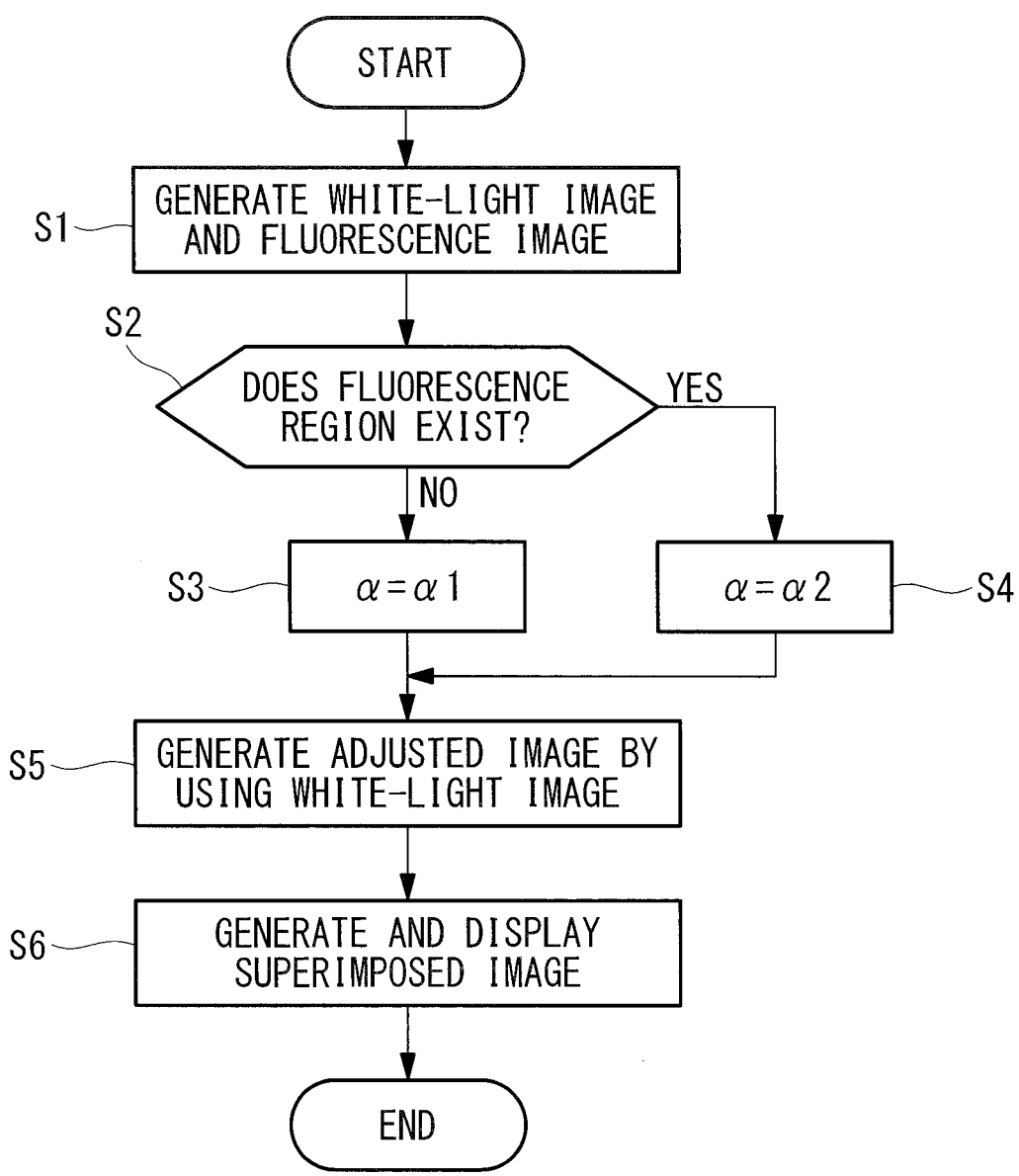
FIG. 2 is a flowchart for explaining image processing performed by an image-processing unit in FIG. 1.

FIG. 2 shows a flowchart for explaining image processing performed by the image-processing unit 6.

In the image-processing unit 6, the white-light-image information S1 is input to the white-light-image generating portion 61, thus generating the white-light image G1, and the fluorescence-image information S2 is input to the fluorescence-image generating portion 62, thus generating the fluorescence image G2 (step S1). Subsequently, whether or not the fluorescence region F exists in the fluorescence image G2 is judged in the fluorescence detecting portion 63 (step S2).

Because the fluorescence region F is not detected in step S2 ("NO" in step S2) in the case in which the affected site Y does not exist in the viewing field, the coefficient α is set to α1 (=1) in the coefficient setting portion 64 (step S3). Therefore, in the white-light-image adjusting portion 65, the white-light image G1 is output to the superimposed-image generating portion 66 as the adjusted image G1' without modification (step S5), and, in the superimposed-image generating portion 66, a superimposed image G3 in which a fluorescence image G2 having almost no gradation values is superimposed on the unprocessed white-light image G1 is generated (step S6). The superimposed image G3 generated at this time is practically equivalent to a raw white-light image G1.

On the other hand, because the fluorescence region F is detected in step S2 ("YES" in step S2) in the case in which the affected site Y exists in the viewing field, the coefficient α is set to α2 (<1) in the coefficient setting portion 64 (step S4). Therefore, in the white-light-image adjusting portion 65, the adjusted image G1' is generated by applying processing for decreasing the gradation values to the white-light image G1 (step S5), and thus, the superimposed image G3 in which the fluorescence image G2 having the original gradation values is superimposed on this adjusted image G1' is generated (step S6). The superimposed image G3 generated at this time is an image in which the fluorescence region F that is bright relative to the white-light image G1 is superimposed on the white-light image G1 having a lower overall brightness. Therefore, the brightness of the fluorescence region F stands out in the superimposed image G3.

As has been described above, with this embodiment, depending on whether or not the fluorescence region F on which the observer focuses exists in the viewing field, the brightness of the white-light image G1 included in the superimposed image G3 is changed. In other words, because an ordinary, clear white-light image G1 is displayed on the monitor 7 in the case in which the fluorescence region F does not exist, the observer can clearly observe the morphology of the biological tissue. On the other hand, in the case in which the fluorescence region F exists, the superimposed image G3 in which the brightness of the white-light image G1 is decreased so that the brightness of the fluorescence region F stands out is displayed on the monitor 7. Therefore, the observer can easily visually recognize the fluorescence region F and, at the same time, he/she can also sufficiently clearly observe the biological tissue that is displayed behind the fluorescence region F.

Note that, in this embodiment, when the fluorescence region F is detected by the fluorescence detecting portion 63, it is preferable that the coefficient setting portion 64 set the coefficient α by taking into account also the number of pixels detected as the fluorescence region F. In other words, the fluorescence detecting portion 63 outputs, to the coefficient setting portion 64, the number of pixels having the gradation values equal to or greater than the gradation value threshold Th. The coefficient setting portion 64 selects α2 only when the number of pixels received from the fluorescence detecting portion 63 is equal to or greater than a predetermined pixel number threshold. On the other hand, even if pixels having the gradation values equal to or greater than the gradation value threshold Th are detected, the coefficient setting portion 64 selects α1 when the number of pixels is less than the predetermined pixel number threshold.

Even in the case in which the affected site Y does not exist in the viewing field, noise having gradation values equal to or greater than the predetermined gradation value threshold Th could occur in the fluorescence image G2. In the case in which such noise is erroneously detected as the fluorescence region F, the brightness of the white-light image G1 unnecessarily fluctuates in the superimposed image G3, thus bothering the observer. Therefore, by decreasing the gradation values of the white-light image G1 only when there are a sufficient number of pixels that exceed the gradation value threshold Th, it is possible to prevent the gradation values of the white-light image G1 from unnecessarily being decreased in response to noise.

Next, modifications of this embodiment will be described.
(First Modification)

Figure 3:
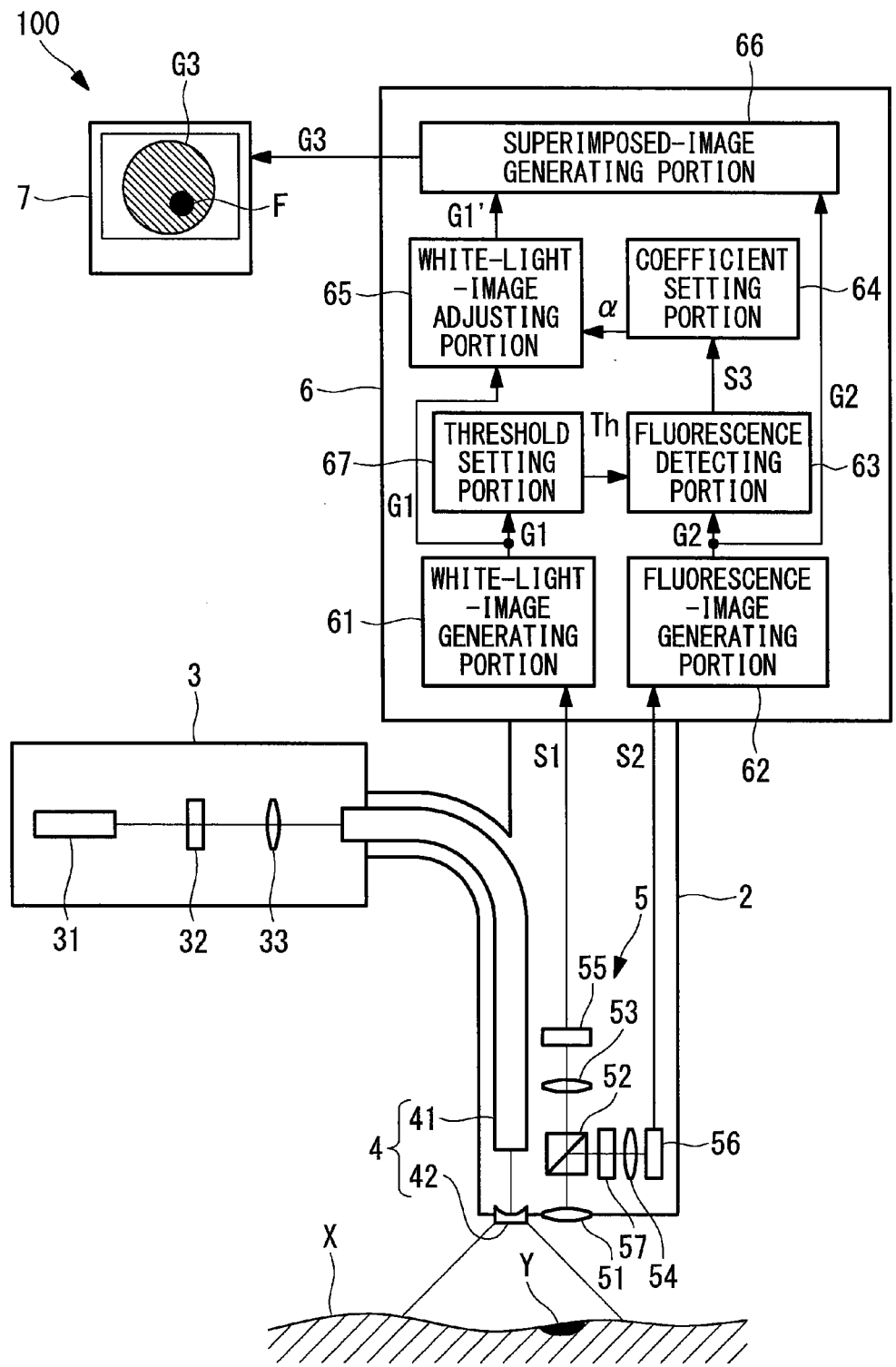
FIG. 3 is an overall configuration diagram of a first modification of the fluorescence observation apparatus in FIG. 1.

As shown in FIG. 3, the fluorescence observation apparatus 100 according to a first modification of this embodiment is additionally provided with a threshold setting portion 67 that sets the gradation value threshold Th for the fluorescence detecting portion 63 based on the gradation values of the white-light image G1.

The threshold setting portion 67 receives the white-light image G1 from the white-light-image generating portion 61, and calculates a representative value m of the gradation values of the white-light image G1. The representative value m is, for example, an average value or a median value of the gradation values of all pixels of the white-light image G1. The threshold setting portion 67 calculates the gradation value threshold Th based on a predetermined function by using the representative value m. Here, the predetermined function is an increasing function in which the gradation value threshold Th increases with an increase in the representative value m.

The gradation values of the white-light image G1 fluctuate overall, depending on the observation distance between the distal end of the inserted portion 2 and the observation subject X, and the overall brightness of the white-light image G1 increases with a decrease in the observation distance. Similarly, the gradation values of the fluorescence image G2 also fluctuate overall, depending on the observation distance, and, even if the intensity of the fluorescence emitted from the observation subject X is the same, the gradation values of the fluorescence region F in the fluorescence image G2 decrease with an increase in the observation distance.

With this modification, the magnitude of the observation distance is judged based on the representative value m of the gradation values of the white-light image G1, the gradation value threshold Th is changed in accordance with the fluctuation of the gradation values of the fluorescence image G2 caused by the changes in the observation distance, and thus, it is possible to enhance the detection precision for the fluorescence region F; as a result, there is an advantage in that a superimposed image G3 in which the brightness of the white-light image G1 is more appropriately adjusted can be presented to the observer.
(Second Modification)

Figure 4:
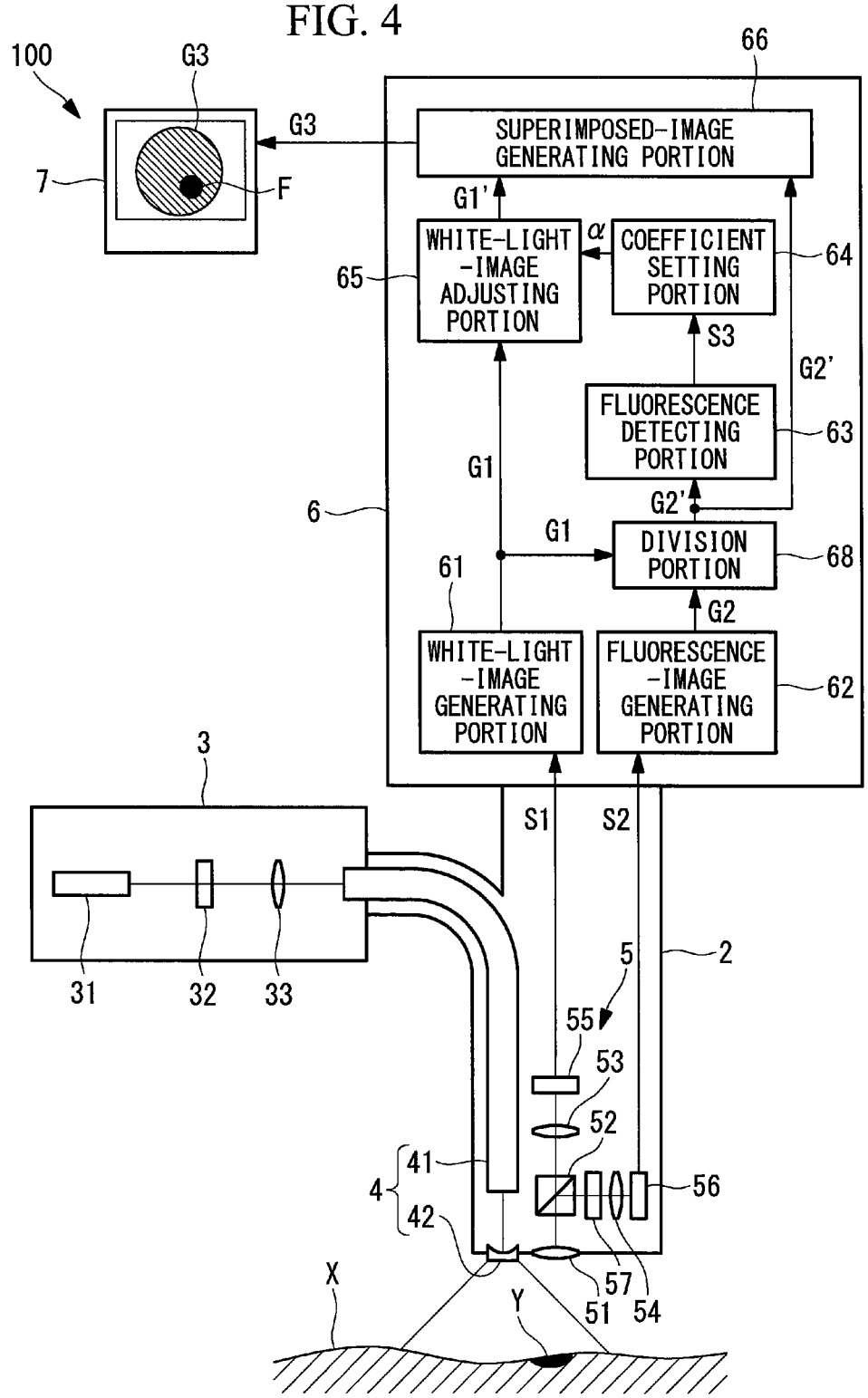
FIG. 4 is an overall configuration diagram of a second modification of the fluorescence observation apparatus in FIG. 1.

As shown in FIG. 4, the fluorescence observation apparatus 100 according to a second modification of this embodiment is additionally provided with a division portion 68 that divides the fluorescence image G2 by the white-light image G1.

The division portion 68 generates a fluorescence image (hereinafter, referred to as a corrected fluorescence image) G2' in which the gradation values are corrected by dividing the gradation values of the individual pixels of the fluorescence image G2 input from the fluorescence-image generating portion 62 by the gradation values of the individual pixels of the white-light image G1 input from the white-light-image generating portion 61. Then, the division portion 68 outputs the generated corrected fluorescence image G2' to the fluorescence detecting portion 63 and the superimposed-image generating portion 66.

The fluorescence detecting portion 63 detects the fluorescence region F in the corrected fluorescence image G2' instead of the fluorescence image G2.

The superimposed-image generating portion 66 generates the superimposed image G3 by using the corrected fluorescence image G2' instead of the fluorescence image G2. In other words, the superimposed-image generating portion 66 uses the gradation values of the corrected fluorescence image G2' as FL in Expression (1).

The gradation values of the white-light image G1 fluctuate depending on the observation angle between the distal end of the inserted portion 2 and the observation subject X in addition to the above-described observation distance. Similarly, the gradation values of the fluorescence image G2 fluctuate depending on the observation distance and the observation angle. Therefore, by dividing the fluorescence image G2 by the white-light image G1, the gradation values of the fluorescence image G2 are normalized, and thus, a corrected fluorescence image G2' from which changes in the gradation values that depend on the observation distance and the observation angle are removed is obtained. By using such a corrected fluorescence image G2', it is possible to enhance the detection precision for the fluorescence region F, and thus, it is possible to provide a superimposed image G3 having greater reliability.

Second Embodiment

Figure 6:
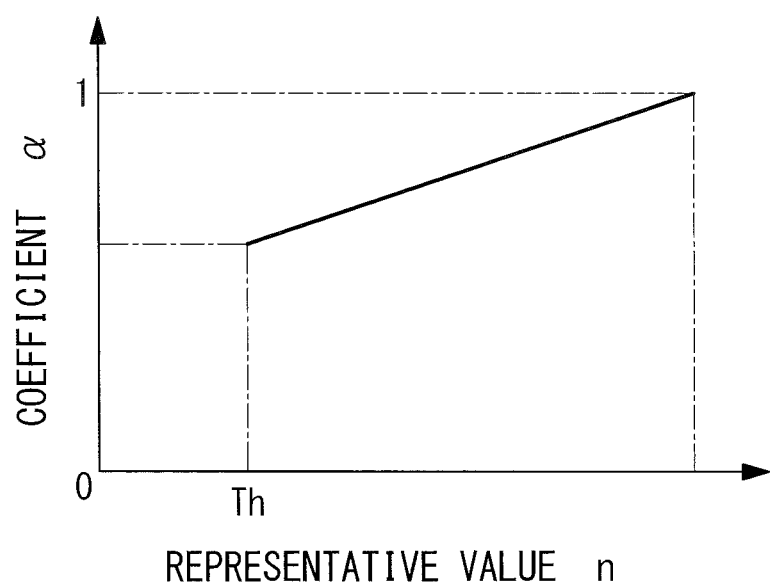
FIG. 6 is a graph of a function used in a coefficient setting portion in FIG. 5, in which the function shows a coefficient α with respect to a representative value n of gradation values of a fluorescence region.
Figure 7:
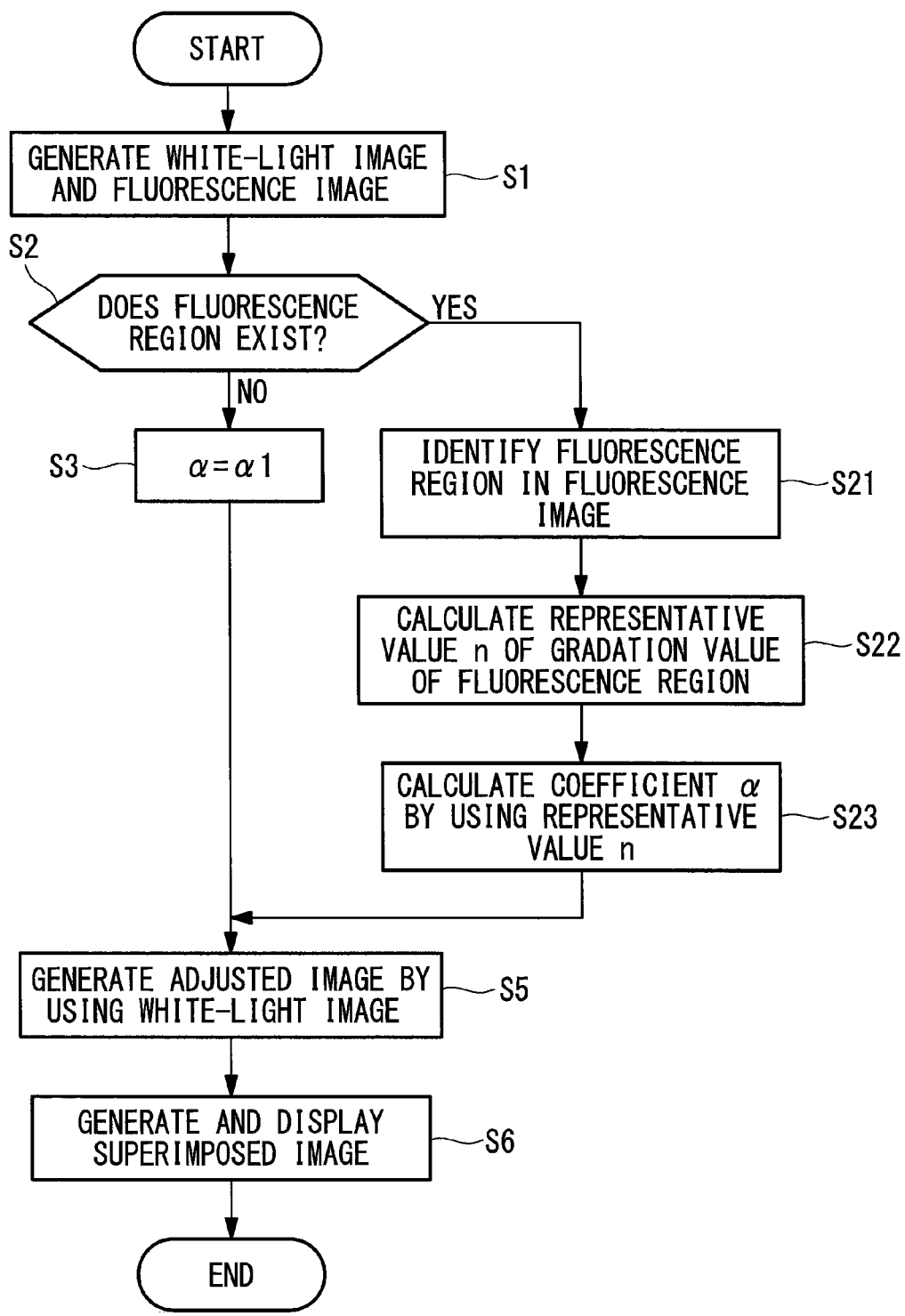
FIG. 7 is a flowchart for explaining image processing performed by an image-processing unit in FIG. 5.

Next, a fluorescence observation apparatus 200 according to a second embodiment of the present invention will be described with reference to FIGS. 5 to 7. In this embodiment, configurations differing from those of the first embodiment will mainly be described, and configurations that are the same as those of the first embodiment will be given the same reference signs and descriptions thereof will be omitted.

Figure 5:
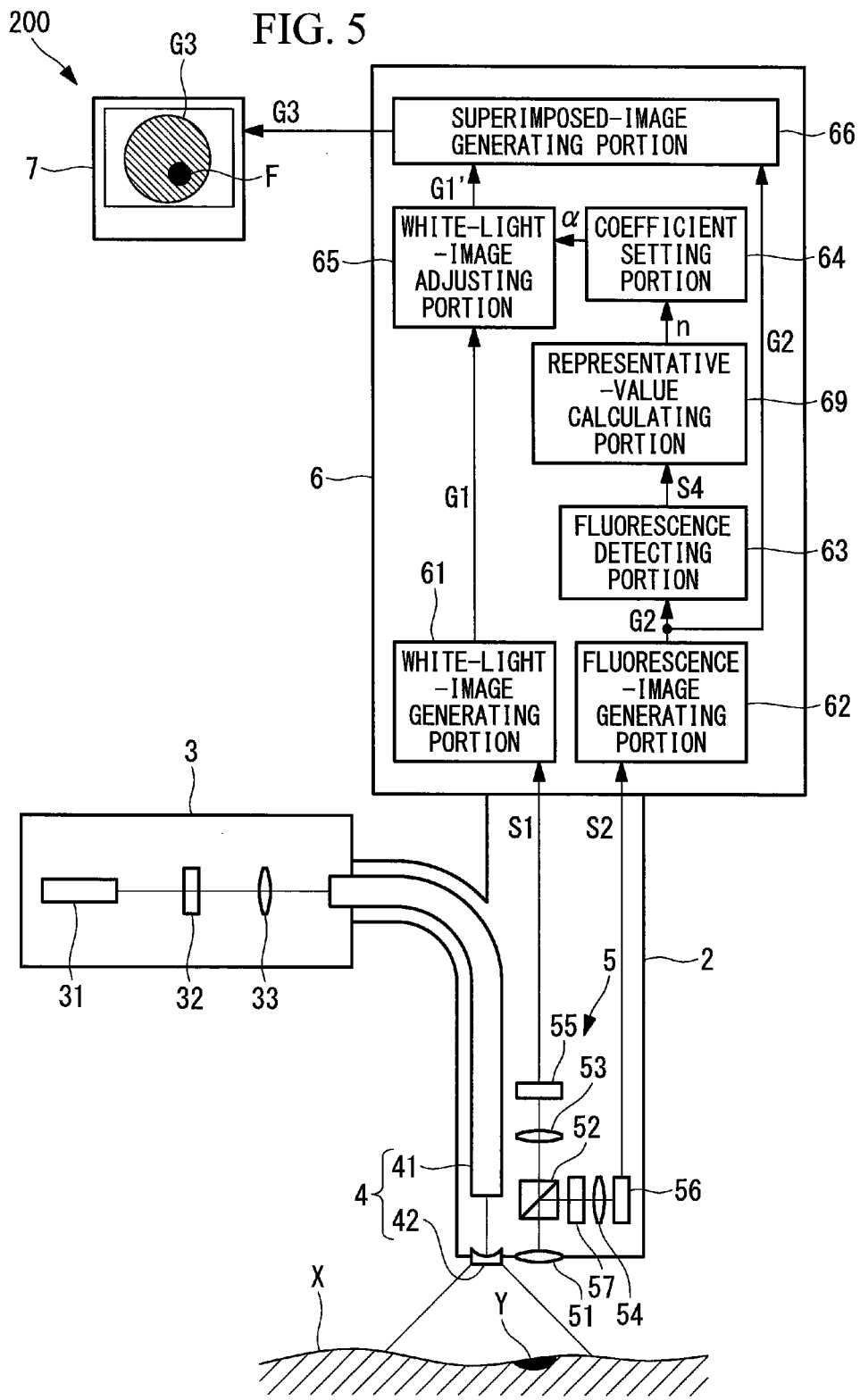
FIG. 5 is an overall configuration diagram of a fluorescence observation apparatus according to a second embodiment of the present invention.

As shown in FIG. 5, the fluorescence observation apparatus 200 according to this embodiment mainly differs from that of the first embodiment in that a representative-value calculating portion 69 that calculates a representative value n of the gradation values of the fluorescence region F detected by the fluorescence detecting portion 63 is additionally provided and that the coefficient setting portion 64 sets the coefficient α in accordance with the representative value n calculated by the representative-value calculating portion 69.

In this embodiment, in the case in which pixels having gradation values equal to or greater than the predetermined gradation value threshold Th exist, the fluorescence detecting portion 63 identifies the corresponding pixels, and outputs gradation values S4 of the identified pixels to the representative-value calculating portion 69.

As the representative value n of the gradation values S4 of the pixels input from the fluorescence detecting portion 63, the representative-value calculating portion 69 calculates, for example, an average value, and outputs the calculated representative value n to the coefficient setting portion 64.

In this embodiment, the coefficient setting portion 64 calculates the value of the coefficient α based on a predetermined function by using the representative value n calculated by the representative-value calculating portion 69 and outputs the calculated value to the white-light-image adjusting portion 65. Here, the predetermined function is an increasing function in which the coefficient α increases with an increase in the representative value n, and is, for example, a linear function, as shown in FIG. 6. The representative value n takes a value equal to or greater than the gradation value threshold Th but equal to or less than the maximum possible value that the gradation values of the fluorescence image G2 could possibly take, and the coefficient α takes a value greater than zero but equal to or less than 1.

Next, the operation of the thus-configured fluorescence observation apparatus 200 will be described.

With the fluorescence observation apparatus 200 according to this embodiment, processing performed in step S2 in the case in which the fluorescence region F is detected differs from that of the first embodiment. As shown in FIG. 7, in the case in which the fluorescence region F exists in the fluorescence image G2 ("YES" in step S2), the fluorescence region F is identified in the fluorescence detecting portion 63 (step S21). Subsequently, the representative value n of the gradation values of the identified fluorescence region F is calculated in the representative-value calculating portion 69 (step S22). Subsequently, the coefficient α in accordance with the representative value n is set in the coefficient setting portion 64 (step S23). The white-light-image adjusting portion 65 generates the adjusted image G1' by using the coefficient α set in step S23 (step S5).

Here, the coefficient α set in the step S23 is a value that reflects the brightness of whole fluorescence region F. Therefore, the degree-of-reduction when decreasing the gradation values of the white-light image G1 in the white-light-image adjusting portion 65 is adjusted in accordance with the brightness of whole fluorescence region F. In other words, in the case in which the fluorescence region F as a whole is sufficiently bright, the coefficient α takes a value closer to 1, and an adjusted image G1' in which the brightness is hardly decreased relative to that of the white-light image G1 is generated. On the other hand, in the case in which the fluorescence region F as a whole is sufficiently dark, the coefficient α takes a lower value, and an adjusted image G1' in which the brightness is sufficiently decreased relative to that of the white-light image G1 is generated.

In the case in which the gradation values of the fluorescence region F are sufficiently high, sufficient visibility of the fluorescence region F is achieved relative to that of the white-light image G1. As has been described above, with this embodiment, the degree-of-reduction of the brightness of the white-light image G1 is adjusted, in accordance with the brightness of the fluorescence region F, to an amount that is necessary and sufficient to achieve sufficient visibility of the fluorescence region F. Thus, there is an advantage in that it is possible to enhance the visibility of the fluorescence region F in the superimposed image G3 and that it is also possible to minimize the degree-of-reduction of the brightness of the white-light image G1 to prevent the image of the subject X in the superimposed image G3 from becoming unclear. Because other operational advantages are the same as those of the first embodiment, descriptions thereof will be omitted.

Note that, in this embodiment, the coefficient setting portion 64 may output the calculated coefficient α to the monitor 7, and the monitor 7 may display the coefficient α.

By doing so, as compared with the ordinary white-light image G1 (in other words, when α=1), the observer can recognize the extent to which the brightness of the adjusted image G1' is decreased in the superimposed image G3 currently displayed on the monitor 7, and thus, there is an advantage in that it is possible to enhance the diagnosis precision based on the superimposed image G3.

Third Embodiment

Next, a fluorescence observation apparatus 300 according to a third embodiment of the present invention will be described with reference to FIGS. 8 to 10. In this embodiment, configurations differing from those of the first and second embodiments will mainly be described, and configurations that are the same as those of the first and second embodiments will be given the same reference signs, and descriptions thereof will be omitted.

Figure 8:
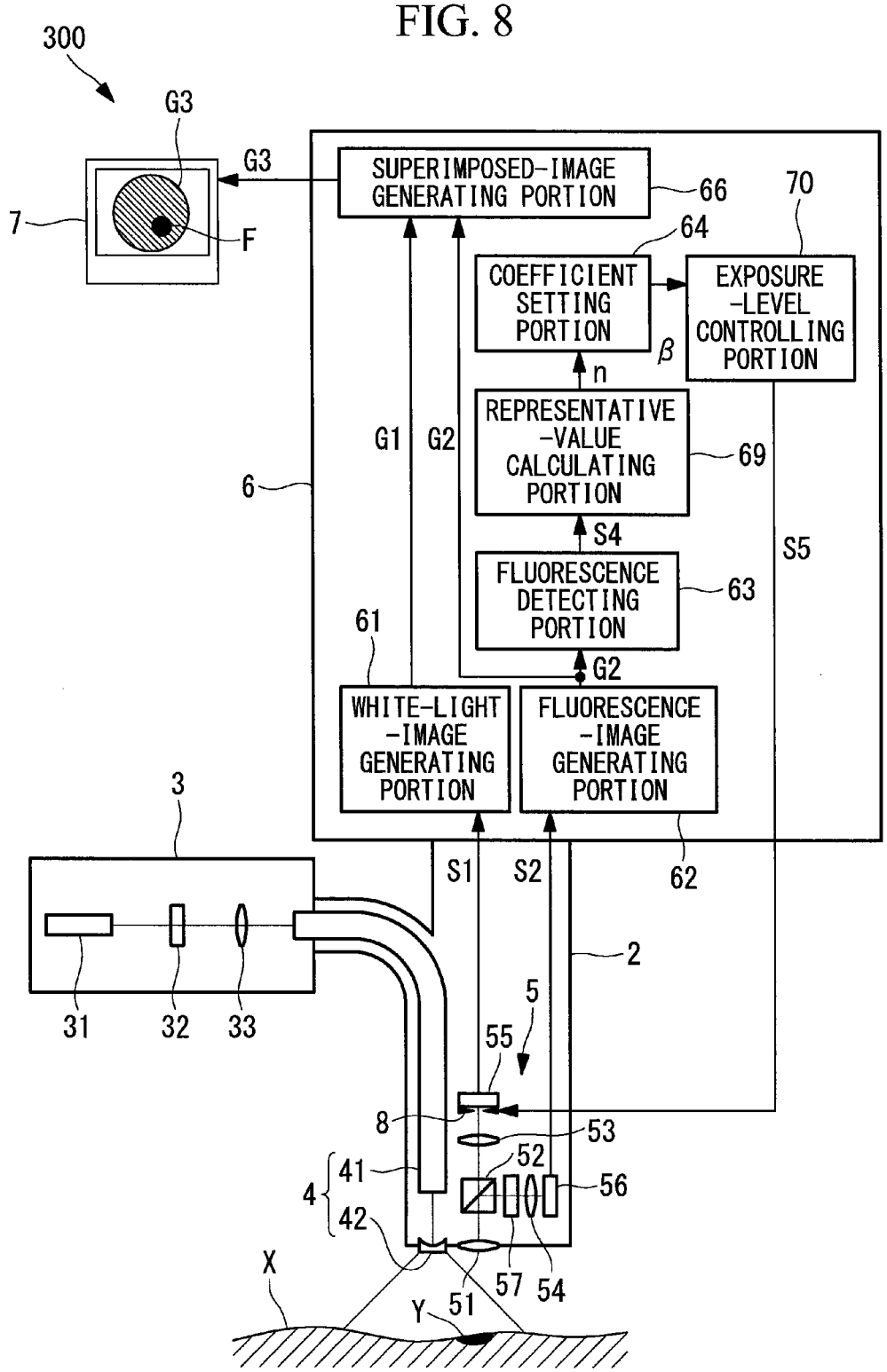
FIG. 8 is an overall configuration diagram of a fluorescence observation apparatus according to a third embodiment of the present invention.
Figure 9:
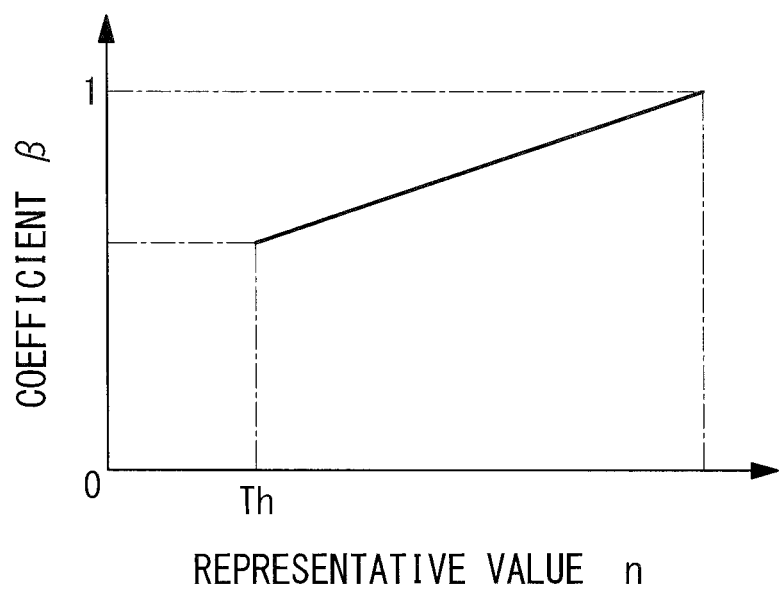
FIG. 9 is a graph of a function used in a coefficient setting portion in FIG. 8, in which the function shows a coefficient β with respect to a representative value n of gradation values of a fluorescence region.

As shown in FIG. 8, the fluorescence observation apparatus 300 according to this embodiment mainly differs from those of the first and second embodiments in that the representative-value calculating portion 69 described in the second embodiment and an exposure-level controlling portion (return-light-image adjusting portion) 70 that controls an aperture stop 8 provided in a stage preceding the image-acquisition device 55 for the white-light image G1 are additionally provided, and that the coefficient setting portion 64 sets a coefficient β related to the aperture diameter of the aperture stop 8 instead of the coefficient α.

The coefficient setting portion 64 calculates the coefficient β based on a predetermined function by using the representative value n calculated by the representative-value calculating portion 69, and outputs the calculated coefficient β to the exposure-level controlling portion 70. Here, the predetermined function is an increasing function in which the coefficient β increases with an increase in the representative value n, and is, for example, a linear function, as shown in FIG. 9. The coefficient β takes a value greater than zero but equal to or less than 1.

The exposure-level controlling portion 70 controls the aperture diameter of the aperture stop 8 by transmitting signals S5 that specify an aperture diameter φ to the aperture stop 8 based on the detection result of the fluorescence detecting portion 63 about the fluorescence region F and the coefficient β input from the coefficient setting portion 64. Specifically, the exposure-level controlling portion 70 keeps the aperture diameter of the aperture stop 8 at a predetermined diameter φ during the normal operation in which the fluorescence region F is not detected by the fluorescence detecting portion 63. On the other hand, in the case in which the fluorescence region F is detected by the fluorescence detecting portion 63, the exposure-level controlling portion 70 controls the aperture diameter of the aperture stop 8 so that a diameter obtained by multiplying the diameter φ for the normal operation by the coefficient β is obtained. For example, in the case in which the coefficient β is 0.8, the aperture stop 8 is controlled so that the aperture diameter becomes 80% of that during the normal operation. In this case, the exposure level in the image-acquisition device 55 for the white light is consequently decreased to about 80% of that during the normal operation.

In this embodiment, the superimposed-image generating portion 66 generates the superimposed image G3 by using, always without modification, the white-light image G1 generated by the white-light-image generating portion 61 and the fluorescence image G2 generated by the fluorescence-image generating portion 62. In other words, in this embodiment, as described below, the white-light image G1 generated by the white-light-image generating portion 61 serves as an adjusted image in which the gradation values have been adjusted. Therefore, regardless of the presence/absence of the fluorescence region F, the superimposed-image generating portion 66 generates the superimposed image G3 in accordance with Expression (1) in which α is set to 1.

Next, the operation of the thus-configured fluorescence observation apparatus 300 will be described.

With the fluorescence observation apparatus 300 according to this embodiment, the processing after judging the presence/absence of the fluorescence region F in step S2 differs from those of the first and second embodiments. As shown in FIG. 10, in the case in which the fluorescence region F is not detected in step S2 ("NO" in step S2), the aperture diameter of the aperture stop 8 is adjusted to the predetermined diameter φ (steps S31 and S36). By doing so, the white-light image G1 to be generated next becomes an image possessing ordinary brightness.

On the other hand, in the case in which the fluorescence region F is detected in step S2 ("YES" in step S2), as in steps S21 to S23 of the second embodiment, the fluorescence region F is identified in the fluorescence detecting portion 63 (step S32), the representative value n of the gradation values of the fluorescence region F is calculated in the representative-value calculating portion 69 (step S33), and the coefficient β in accordance with the representative value n is set in the coefficient setting portion 64 (step S34). Then, the aperture diameter of the aperture stop 8 is adjusted in accordance with the coefficient β so as to be smaller than that during the normal operation (steps S35 and S36). By doing so, the white-light image G1 to be generated next becomes an image in which the brightness is decreased as compared with that during the normal operation. Specifically, by decreasing the degree-of-opening of the aperture stop 8 positioned at the stage preceding the image-acquisition device 55 for white light, while leaving an aperture stop (not shown) positioned at a stage preceding the image-acquisition device 56 for fluorescence with the degree-of-opening thereof unchanged, it is possible to decrease the relative brightness of the white-light image G1 as compared with that of the fluorescence image G2 by decreasing only the amount of the white light received from among the light (reflected/absorbed light) emitted from the same site.

As has been described above, with this embodiment, it is possible to adjust the brightness of the white-light image G1 in accordance with the presence/absence of the fluorescence region F also by decreasing the exposure level in the image-acquisition device 55, instead of decreasing the gradation values of the white-light image G1 by means of computational processing, as in the first and second embodiments. By doing so, it is possible to achieve the same operational advantages as in the first embodiment. Furthermore, by adjusting the aperture diameter of the aperture stop 8 in accordance with the brightness of the fluorescence region F, there is an advantage in that, as with the second embodiment, it is possible to minimize the deterioration of the visibility of the white-light image G1 in the superimposed image G3 by adjusting the degree-of-reduction of the brightness of the white-light image G1 to an amount that is necessary and sufficient to achieve sufficient visibility of the fluorescence region F. Furthermore, because the white-light image G1 can be used without modification to generate the superimposed image, the computational processing can be simplified.

Note that, in this embodiment, although the gradation values of the white-light image G1 are decreased by decreasing the amount of light that enters the image-acquisition device 55 by using the aperture stop 8, alternatively, the exposure time in the image-acquisition device 55 may be decreased. The adjustment of the exposure time is performed by, for example, the exposure-level controlling portion 70 by controlling the amount of time by which an electronic shutter (not shown) provided in the image-acquisition device 55 is opened. By doing so also, it is possible to generate a white-light image G1 in which the gradation values are decreased as compared with those during the normal operation by using the white-light-image generating portion 61, as with the case in which the aperture stop 8 is used.

Fourth Embodiment

Figure 11:
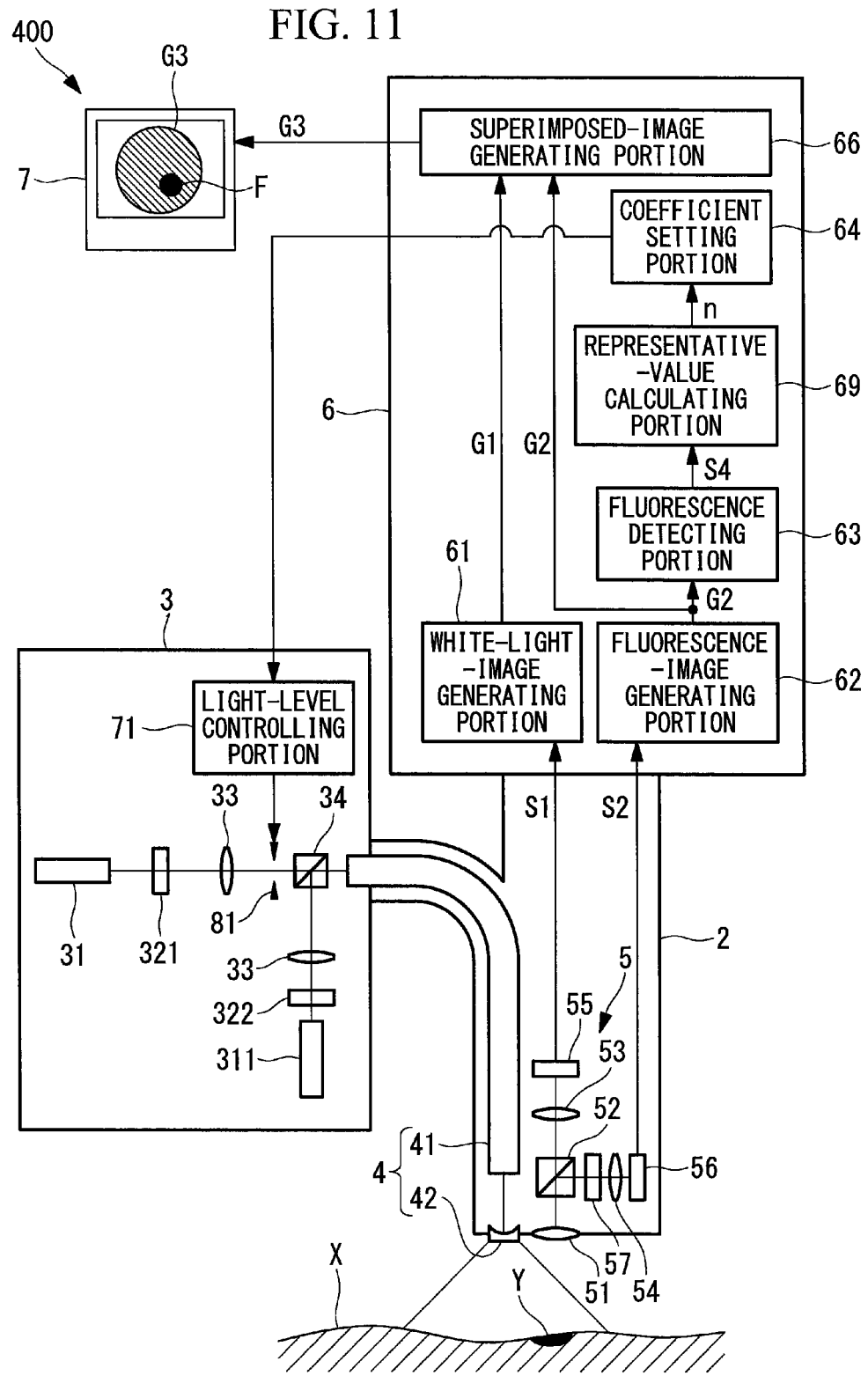
FIG. 11 is an overall configuration diagram of a fluorescence observation apparatus according to a fourth embodiment of the present invention.

Next, a fluorescence observation apparatus 400 according to a fourth embodiment of the present invention will be described with reference to FIG. 11. In this embodiment, configurations differing from those of the first to third embodiments will mainly be described, and configurations that are the same as those of the first embodiment will be given the same reference signs and descriptions thereof will be omitted.

The fluorescence observation apparatus 400 according to this embodiment is the same as that of the third embodiment in that the gradation values of the white-light image G1 are decreased by adjusting the exposure level in the image-acquisition device 55. However, as shown in FIG. 11, the fluorescence observation apparatus 400 of this embodiment is provided with an aperture stop 81 at the light source 3, instead of the stage preceding the image-acquisition device 55, and the light-level controlling portion (exposure-level controlling portion, return-light-image adjusting portion) 71 changes the amount of illumination light radiated onto the observation subject X by controlling the aperture stop 81.

In this embodiment, the light source 3 is additionally provided with another xenon lamp 311 and a beam splitter 34. The beam splitter 34 combines the light emitted from the two xenon lamps 31 and 311 in the entrance optical axis leading to the light-guide fiber 41. Note that the xenon lamps 31 and 311 may be other types of lamp light sources or semiconductor light sources, such as LEDs or the like. In addition, the xenon lamps 31 and 311 may be of the same type or of mutually different types.

The light source 3 is provided with a first filter 321 and a second filter 322 instead of the filter 32. The first filter 321 extracts illumination light (for example, a wavelength band from 400 nm to 700 nm) from the light emitted from the first xenon lamp 31. The second filter 322 extracts excitation light (for example, a wavelength band from 700 nm to 740 nm) from the light emitted from the second xenon lamp 311.

The aperture stop 81 is disposed between the first filter 321 and the beam splitter 34 and changes the light level of only the illumination light in the light that enters the light-guide fiber 41.

Except for controlling the aperture stop 81 instead of the aperture stop 8, the light-level controlling portion 71 is the same as the exposure-level controlling portion 70 of the third embodiment. In this embodiment, by decreasing the aperture diameter of the aperture stop 81, the amount of the illumination light radiated onto the observation subject X and the amount of the white light collected by the objective lens 51 are decreased, and, accordingly, the exposure level in the image-acquisition device 55 is decreased.

Figure 10:
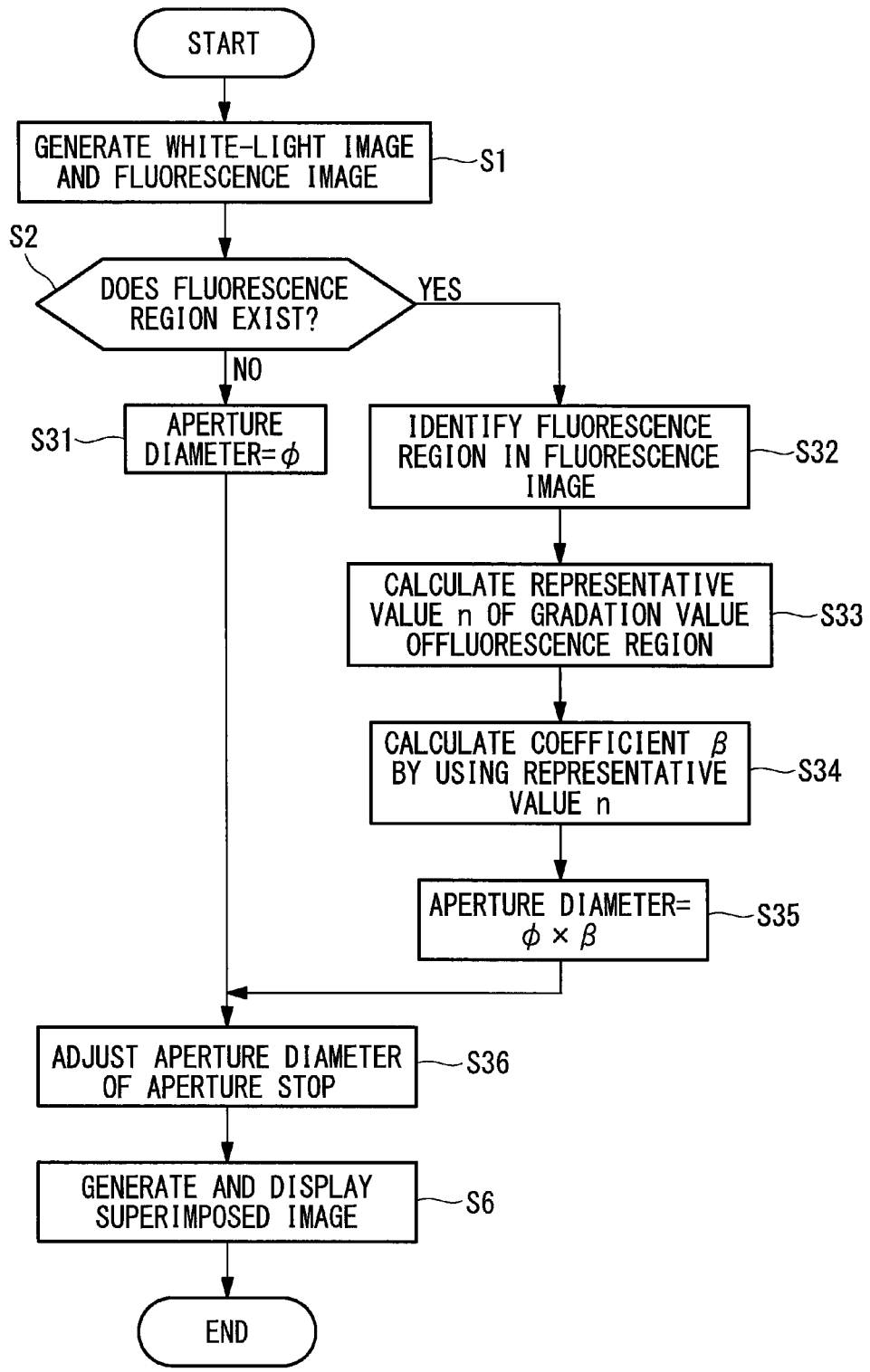
FIG. 10 is a flowchart for explaining image processing performed by an image-processing unit in FIG. 8.

Descriptions of the operation and the operational advantages of the fluorescence observation apparatus 400 according to this embodiment will be omitted because they are the same as those of the fluorescence observation apparatus 300 of the third embodiment described above, except for the difference in terms of the aperture stop 81 in which the aperture diameter is adjusted in steps S31, S35, and S36 in FIG. 10.

Fifth Embodiment

Next, a fluorescence observation apparatus 500 according to a fifth embodiment of the present invention will be described with reference to FIGS. 12 and 13. In this embodiment, configurations differing from those of the first to fourth embodiments will mainly be described, and configurations that are the same as those of the first embodiment will be given the same reference signs and descriptions thereof will be omitted.

Figure 12:
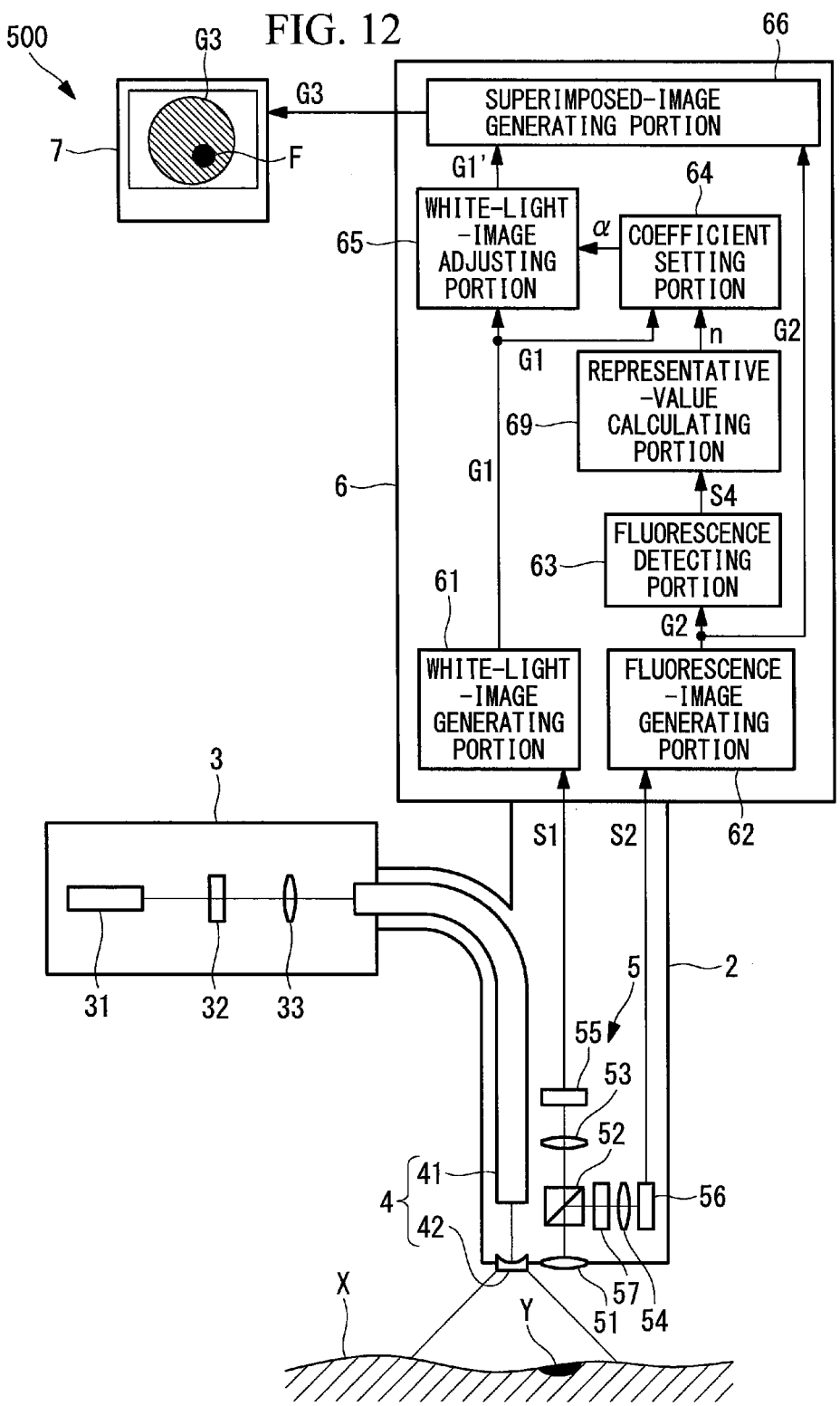
FIG. 12 is an overall configuration diagram of a fluorescence observation apparatus according to a fifth embodiment of the present invention.
Figure 13:
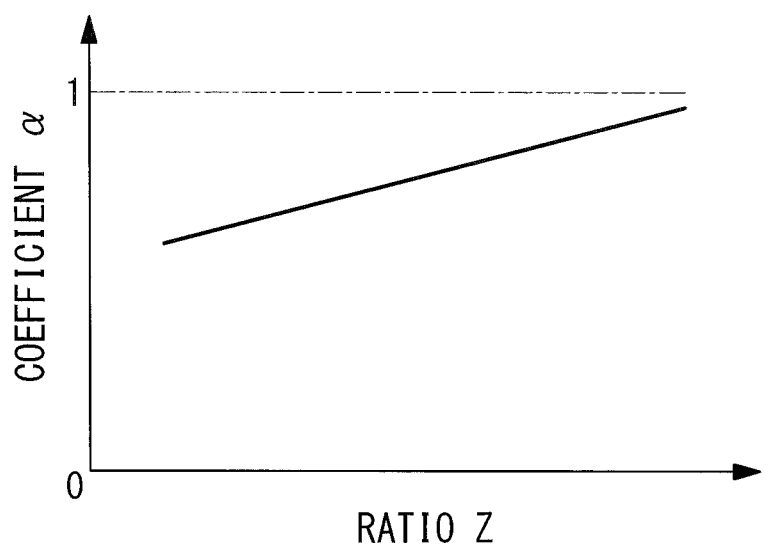
FIG. 13 is a graph of a function used in a coefficient setting portion in FIG. 12, in which the function shows a coefficient α with respect to a ratio Z.

As shown in FIG. 12, the fluorescence observation apparatus 500 according to this embodiment mainly differs from those of the first to fourth embodiments in that the coefficient setting portion 64 sets the coefficient $\alpha$ ($0<\alpha\leq1$) by taking into account also the color components of the white-light image G1.

In this embodiment, the white-light-image generating portion 61 outputs the white-light image G1 also to the coefficient setting portion 64 in addition to the white-light-image adjusting portion 65.

Before setting the coefficient $\alpha$, the coefficient setting portion 64 judges the color tone of the white-light image G1 input from the white-light-image generating portion 61.

Specifically, the coefficient setting portion 64 calculates an average value <G'> and an average value <R> by using the white-light image G1. The average value <G'> is the sum of an average value <G> of the gradations values of the G components in the white-light image G1 and the representative value n calculated by the representative-value calculating portion 69. The average value <R> is the average value of the gradation values of the R components in the white-light image G1.

Subsequently, the coefficient setting portion 64 calculates a ratio Z (=<G'>/<R>) between the average value <G'> and the average value <R>. Then, the coefficient setting portion 64 calculates the coefficient $\alpha$ based on a predetermined function by using the ratio Z, and outputs the coefficient $\alpha$ to the white-light-image adjusting portion 65. Here, the predetermined function is an increasing function in which the coefficient $\alpha$ increases with an increase in the ratio Z, and is, for example, a linear function, as shown in FIG. 13.

The visibility of the fluorescence region F in the superimposed image G3 also depends on the contrast between the hue of the biological tissue X and the color in which the fluorescence region F is displayed.

The above-described ratio Z expresses the contrast of the hue of the biological tissue relative to green, which is the color in which the fluorescence region F is displayed. Specifically, in the case in which the redness of the biological tissue is high mainly due to the effect of blood, the ratio Z and the coefficient $\alpha$ are decreased, and the degree-of-reduction of the gradation values of the white-light image G1 is increased. On the other hand, in the case in which the redness of the biological tissue is low because the surface of the biological tissue is covered with fat or the like, the ratio Z and the coefficient $\alpha$ are increased, and the degree-of-reduction of the gradation values of the white-light image G1 is decreased.

As has been described above, with this embodiment, by taking into consideration also the color tone of the white-light image G1, the degree-of-reduction of the brightness of the white-light image G1 is adjusted to an amount that is necessary and sufficient to achieve sufficient visibility of the fluorescence region F, and thus, there is an advantage in that it is possible to enhance the visibility of the fluorescence region F in the superimposed image G3, and it is also possible to minimize the degree-of-reduction of the brightness of the white-light image G1 to prevent the image of the subject X in the superimposed image G3 from becoming unclear.

REFERENCE SIGNS LIST 100, 200, 300, 400, 500 fluorescence observation apparatus
2 inserted portion
3 light source
31, 311 xenon lamp
32, 321, 322 filter
33 coupling lens
34 beam splitter
41 light-guide fiber
42 illumination optical system
51 objective lens
52 dichroic mirror
53, 54 focusing lens
55, 56 image-acquisition device
57 excitation-light cut filter
4 illumination unit
5 image-acquisition unit
6 image-processing unit
61 white-light-image generating portion (return-light-image generating portion)
62 fluorescence-image generating portion
63 fluorescence detecting portion
64 coefficient setting portion
65 white-light-image adjusting portion (return-light-image adjusting portion)
66 superimposed-image generating portion
67 threshold setting portion
68 division portion
69 representative-value calculating portion
70 exposure-level controlling portion (return-light-image adjusting portion)
71 light-level controlling portion (exposure-level controlling portion, return-light-image adjusting portion)
7 monitor
8, 81 aperture stop

The invention claimed is:

1. A fluorescence observation apparatus comprising:
a light source configured to radiate illumination light and excitation light onto a subject; and
a processor comprising hardware, wherein the processor is configured to:
generate a return-light image in which return light emitted from the subject due to the irradiation with the illumination light from the light source is captured;
generate a fluorescence image in which fluorescence emitted from the subject due to the irradiation with the excitation light from the light source is captured;
perform a detection of a fluorescence region having gradation values equal to or greater than a predetermined gradation value threshold in the fluorescence image;
adjust gradation values of the return-light image;
generate a superimposed image in which the return-light image, in which the gradation values have been adjusted, and the fluorescence image are superimposed; and
set a degree-of-reduction, by which the gradation values of the return-light image are adjusted, based on a detection result of the detection of the fluorescence region,
wherein, in the case in which the fluorescence region is detected, set the degree-of-reduction so that gradation values of the return-light image are decreased as compared with the case in which the fluorescence region is not detected.

2. The fluorescence observation apparatus according to claim 1,
wherein the processor is configured to set a coefficient that is greater than zero but less than 1, and, in the case in which the fluorescence region is detected, multiply the gradation values of the return-light image by the coefficient set to adjust the gradiation values of the return-light image.

3. The florescence observation apparatus according to claim 1,
wherein the processor is configured to:
control an image sensor to capture the return light;
set a degree-of-reduction by which an exposure level in the image sensor for the return light is decreased; and
in the case in which the fluorescence region is detected, decrease the exposure level in the image sensor in accordance with the degree-of-reduction set.

4. The fluorescence observation apparatus according to claim 3,
wherein the processor is configured to control at least one of an amount of the return light that enters the image sensor, an exposure time in the image sensor, and an amount of the illumination light radiated onto the subject.

5. The fluorescence observation apparatus according to claim 1,
wherein the processor is configured to decrease the degree-of-reduction, by which the gradation values of the return-light image are decreased, with an increase in the gradation values of the fluorescence region detected.

6. The fluorescence observation apparatus according to claim 1,
wherein the processor is configured to change, in accordance with a color tone of the return-light image, the degree-of-reduction by which the gradation values of the return-light image are adjusted.

7. The fluorescence observation apparatus according to claim 1,
wherein the processor is configured to decrease the gradation values of the return-light image only when a number of pixels comprising the fluorescence region detected is equal to or greater than a predetermined pixel number threshold.

* * * * *